(12) United States Patent
Dietlin et al.

(10) Patent No.: US 6,992,218 B2
(45) Date of Patent: Jan. 31, 2006

(54) METHOD FOR OBTAINING AQUEOUS FORMULATIONS OF OXIDATION-SENSITIVE ACTIVE PRINCIPLES

(75) Inventors: Francois Dietlin, La Vesinet (FR); Daniele Fredj, Gif sur Yvette (FR)

(73) Assignee: Pharmatop SCR (FR)

( * ) Notice: Subject to any disclaimer, the term of this patent is extended or adjusted under 35 U.S.C. 154(b) by 0 days.

(21) Appl. No.: 10/332,060

(22) PCT Filed: Jun. 6, 2001

(86) PCT No.: PCT/FR01/01749

§ 371 (c)(1),
(2), (4) Date: Aug. 4, 2003

(87) PCT Pub. No.: WO01/93830

PCT Pub. Date: Dec. 13, 2001

(65) Prior Publication Data

US 2004/0054012 A1 Mar. 18, 2004

(30) Foreign Application Priority Data

Jun. 6, 2000 (FR) .......................... 00 07231

(51) Int. Cl.
C07C 209/90 (2006.01)

(52) U.S. Cl. ........................ 564/4; 564/5; 564/6; 564/7; 564/223; 514/617

(58) Field of Classification Search .................... 564/4, 564/5, 6, 7, 223; 514/617
See application file for complete search history.

(56) References Cited

U.S. PATENT DOCUMENTS 6,028,222 A * 2/2000 Dietlin et al. .................. 564/4

* cited by examiner

Primary Examiner—Shailendra Kumar
(74) Attorney, Agent, or Firm—Charles A. Muserlian

(57) ABSTRACT

A method for obtaining aqueous formulations with easily oxidizable active principles, notably phenols, stable over a prolonged period, comprising subjecting them to extreme deoxygenation by bubbling with an inert gas and/or placing wider vaccum, protecting them against possible resorption of oxygen by keeping them under an inert gas atmosphere, by filling, under inert gas, into bottles previously cleared of air by insufflation with inert gas, then subjecting them, while stoppering, to low pressure as obtained in the bottle, of 65,000 Pa maximum, to obtain aqueous solutions having a residual oxygen concentration in the solution below 2 ppm, and preferably of the order of 1 ppm and even 0.5 ppm useful as injectable preparations having an oxygen concentration in the solution below 2 ppm.

19 Claims, No Drawings

METHOD FOR OBTAINING AQUEOUS FORMULATIONS OF OXIDATION-SENSITIVE ACTIVE PRINCIPLES

This application is a 371 of PCT/FR01/01749 filed Jun. 6, 2001.

The object of the present invention is a new method for producing injectable aqueous solutions with active principles, in particular active principles which are useful in therapeutics and susceptible to oxygen, and also a procedure for preparation of these methods of packaging, and their utilization.

Its object is, more precisely, a new method for aqueous formulations with active principles susceptible to oxidation which can notably be utilized in injectable preparations being stable over a long period, and containing, for example, phenolic or polyphenolic substances, amino alcohols or sulphur-containing substances.

Aqueous solutions with active principles traditionally have different applications, notably in therapeutics, in particular in the form of injectable solutions intended for humans or animals. However, it happens that some of these active principles present problems of stability in solution. These problems may be connected with the fact that the active principles are susceptible to oxidation and form undesired degradation products by reaction with the oxygen in the air, or above all with the oxygen dissolved in the aqueous solution. Other active principles are indirectly susceptible to oxygen, i.e. whilst being kept they are likely to form, by chemical reactions, oxidizable derivatives. These derivatives, by reacting with oxygen, then lead to the formation of undesired secondary products. This is the case, in particular, with paracetamol. The Applicants have, in fact, demonstrated the fact that paracetamol, in aqueous solution, undergoes hydrolysis on the one hand, and on the other hand, degrades to form a quinone-imine susceptible to polymerization into nitrogenous polymers. The derivatives resulting from these reactions are themselves also susceptible to oxidation and form undesired secondary products.

The secondary products formed by reaction of the oxygen with these active principles, or their derivatives, leads to numerous disadvantages such as, for example, a loss of activity or the production of allergenic products.

In fact, as a result of degradation by oxidation, the titre of active principle in the aqueous solution is considerably reduced, in an uncontrollable manner, and poses a major problem, especially when these solutions are used in therapeutics, more particularly in the form of injectable solutions, when it is important that the dose of active principle is precisely determined.

Moreover, the oxidation products lead to the formation of coloured compounds, thus making the aqueous solution unsuitable for therapeutic applications.

In addition, the formation of secondary products may further increase as a result of a rise in temperature, which, consequently, may cause heat-sterilization of the aqueous solutions with these active principles, impossible, or at least difficult.

Here and in the following text, the term "phenolic active principle susceptible to oxidation" means any substance, which may or may not be medicinal, comprising a phenolic structure and/or functions supported by the phenolic structure which react easily with oxygen, and which degrades forming oxidation products, coloured or colourless, or hydrolysis products or polymerization products.

The active principles susceptible to oxygen are essentially organic substances bearing oxidizable functions, amongst which the following may in particular be cited: phenols, polyphenols, aminophenols, phenolic alcohols and phenolic ketones, as well as aromatic amines or partially hydrogenated cyclical structures such as derivatives of anthraquinone. The following ones may also be cited:compounds with an enolic structure or with an aldehyde function, or a ketone function or an alcohol function.

Aminosides which are also susceptible to the presence of oxygen may also be cited.

Amongst the easily oxidizable active principles that will be incorporated into the aqueous solutions of the invention, the following may be cited more particularly: phenols or aminophenols, such as paracetamol, epinephrine, norepinephrine, adrenalone, isoprenaline, orciprenaline, isoxuprine, phenylephrine or dobutamine; the following will be cited as aromatic amines: procaine, bupivacaine, tetracaine, butoform, L-dopa or Carbidopa; the following one will be cited as aminoketones:Propaphenone; the following ones will be cited as aminoglucosides: the gentamycines, amikacine, dibekacine, netilmycin, sisomycin, tobramycin, micronomycine; as phenothiazines, promethazine; as hydroaromatic molecules, riboflavin, 9-amino dihydro acridine; further cortisonic derivatives may be cited, such as dexamethasone, betamethasone, triamcinolone, fluocinonide, flunisolide, fluocinolone acetonide, fluocortolone, Clobetasone and their derivatives, beclometasone and its esters; Tetracycline derivatives, such as Doxycycline or Minocycline.

For the purpose of improving the stability of such medicinal active principles which are susceptible to oxidation, and thus to overcome the disadvantages described above, a proposal has already been made to prevent the action of the oxygen, either by eliminating the oxygen, or by neutralizing it, or again by combining both these types of operation.

Several methods have been used for this purpose:

a) elimination of the oxygen by raising the temperature of the aqueous solution, by putting the aqueous solution under vacuum or by bubbling an inert gas such as nitrogen, carbon dioxide or argon through the solution.

However these methods have the disadvantage of allowing only a partial and insufficient elimination of the oxygen, or requiring a considerable amount of time. The bubbling of nitrogen, the method most practised within the pharmaceuticals industry, only allows the oxygen content to be reduced to values of the order of 2 ppm maximum.

b) neutralization of the oxygen dissolved in the aqueous solution, by the addition to the latter of an antioxidant such as a thiol or sulphur anhydride derivatives such as the sulphites, bisulphites or alkali metal metabisulphites.

c) a combination of the elimination of oxygen and the addition of an antioxidant. A method of this type has been described by the Applicants in the French patent 2.751.875.

All the above methods have a certain efficacy. However, oxygen shows a very great facility to dissolve in water, making it necessary to ensure that the solution, once deoxygenated, does not subsequently come into contact with atmospheric air, otherwise the advantage of having previously eliminated the oxygen will be lost.

Within the framework of the industrial manufacture of injectable solutions, it has been easy to deoxygenate bulk solutions in air-tight tanks and thus to keep them away from the air. However, during subsequent bottle or bag filling and packaging operations, it is difficult to keep the solutions totally away from air. In spite of precautions that may be taken for this purpose, especially filling and packaging the bottles with the addition of inert gas, once packaged, the solutions can may once again contain, or fix, or take up significant quantities of dissolved oxygen.

If these solutions have to be heat-sterilized, especially at high temperatures in the region of 120° C., the residual quantity of dissolved oxygen can easily react with the active principle susceptible to oxidation, resulting in its total or partial degradation.

In effect it has been found that the presence of any oxygen is harmful and that infinitesimal quantities are sufficient to bring about an oxidation reaction, especially at sterilization temperature. The residual oxygen concentration limit present in the medium, likely to produce an oxidizing effect, is of the order of 2 ppm.

The applicants have thus made use of a method for stabilizing of the solutions of phenolic, easily oxidizable substances, in which deoxygenation has previous been completed to a degree that would avoid the possibility of this degradation occurring.

It is known, moreover, that the utilization of antioxidants is not always purely advantageous. Thus, the antioxidants used gradually degrade, which makes it necessary to add relatively large quantities of them to ensure satisfactory protection of the active principle.

It is also possible to combine the elimination of oxygen with the addition of an antioxidant.

Complementary tests have shown that the problem of stabilization of the formulations according to the invention was appreciably more complex than anticipated, and it has notably been established that, without antioxidant, an essentially deoxygenated solution became pink in colour after a certain time at ambient temperature. In this respect it has been observed that injectable solutions which are not completely deoxygenated do not become appreciably coloured if an α-hydroxypolycarboxylic acid is previously added to the solution, in particular the addition of citric acid, or an alkaline citrate, or a mixture of the two, makes it possible to slow down the appearance of a coloration.

In addition, it has emerged that it is possible to complete the deoxygenation of a solution of a substance susceptible to oxidation by the use of vacuum. This results is a greater stability of the antioxidant and less formation of secondary products resulting from oxidative degradation, notably after several sterilization cycles.

The α-hydroxypolycarboxylic acids and their salts, play an important role. They do not act by stabilizing the pH, nor by playing a role capturing free radicals. They advantageously replace polyhydroxylated compounds such as sorbitol or mannitol.

In the particular case of paracetamol, a mixture of trisodic citrate and citric acid is preferably used, in a quantity sufficient to obtain a pH value of the order of 5 to 6, and preferably 5.5.

The object of the present invention is therefore a procedure for preparation of formulations of aqueous solutions with phenolic active principles, in particular active principles susceptible to oxidation, like paracetamol, making it possible to confer a high degree of stability over the course of time.

A further object of the present invention consists of the utilization of these formulations for the production of injectable aqueous solutions intended for humans or animals, containing an added phenolic active principle to which an anti-inflammatory agent and/or central analgesic may or may not be added.

The object of the invention is specifically a method for producing an aqueous formulations containing easily oxidizable phenolic active principles, which are stable over a long period of time, possibly containing antioxidants, characterized in that they are obtained by submitting them to extreme deoxygenation either by bubbling of an inert gas, or by placing under vacuum, then protecting them from possible resorption of oxygen during the course of production, by keeping them in an inert gas atmosphere, by packaging them into bottles previously cleared of air by insufflation with inert gas, and notably topping gas which is heavier than air, such as argon, then in that, at the moment of stoppering, they are subjected to a reduction in pressure, so that a pressure is obtained, which is lower than atmospheric pressure, of 65,000 Pa maximum, preferably between 5,000 and 50,000 Pa, to obtain an aqueous solution having an oxygen concentration in the solution below 2 ppm.

According to another aspect of the invention, the invention consists of a method for preparing of a formulation as previously described, which includes the following stages:

a) an aqueous solution with at least one active principle is subjected to extreme, and possibly complete, deoxygenation, b) under an inert gas atmosphere, part or all of the deoxygenated aqueous solution is introduced into a container previously cleared of the air contained therein, c) the container is stoppered under an inert gas atmosphere, in such a way as to create within the container a maximum pressure of 65,000 Pa.

The aqueous solution is preferably deoxygenated by bubbling through an inert gas, such as nitrogen. The bubbling process can be continued until a content of less than 2 ppm is obtained, preferably a content of 1–0.5 ppm, and particularly even 0.05 ppm of oxygen in the aqueous solution. The deoxygenated solution thus obtained can then be conveyed, safe from the air, into a filling machine, to be distributed into containers such as flasks, ampoules or bottles.

The aqueous solution is introduced into the container under an inert gas atmosphere, such as nitrogen. Before the aqueous solution with active principle is introduced into the container, the latter is cleared of the air contained therein, for example by insufflation of an inert gas, preferably an inert gas heavier than air, such as argon, so that the latter is not immediately replaced by air in accordance with Archimedes' principle.

Once the containers have been filled, with constant insufflation of an inert gas, the bottles are stoppered under an extreme vacuum to keep them, after stoppering, at a pressure of 65,000 Pa or below, preferably between 5,000 et 50,000 Pa. To do this, known means can be utilized, such as placing a vacuum bell-jar over the neck of the container, immediately after the stopper is put in. After being placed in hermetic contact, the inside of the bell-jar is placed under a vacuum, for example by linking it to a container under vacuum. The stopper of the container is raised and the gas rising above the solution is aspirated. The stopper is then replaced in the container and the latter can be hermetically sealed, for example by fitting on a capsule, then crimping. The container, once stoppered, can be subjected to a sterilization process, in particular sterilization by autoclaving or irradiation.

The aqueous solution containing an active principle can be subjected to sterilization by sterilising filtration before this solution is introduced into the container. The solution is then introduced into the container, preferably under aseptic conditions, under an inert gas, the latter advantageously being sterile.

The inert gas preferably used in the method according to the invention for bubbling is nitrogen, that used for topping is argon, which is heavier than air. Xenon or neon can also be used.

After the bottles have been filled, with constant insufflation of an inert gas, with the solution of easily oxidizable substance, the bottle is stoppered under an extreme vacuum, to maintain in the bottles after stoppering, a low pressure of more than 300 mm of mercury, or a maximum pressure of 65,000 Pa.

According to the invention procedure, the low pressure prevailing in the bottle promotes the elimination of the oxygen still present in the solution and this constitutes a distinct advantage.

This elimination makes it possible to reduce the quantity of antioxidant necessary for protection of the active principle, or even avoid adding it. It also allows heat-sterilization of solutions that could not be sterilized previously due to degradation of the active principle and/or antioxidant by oxidation during this operation. This reduction in the quantity of antioxidant may also allow these solutions to be stabilized for longer periods.

Thus, French patent 2.751.875 mentions that aqueous solutions of paracetamol are stable for 48 hours at ambient temperature, under light, and at 70° C. in darkness, if they are subjected to bubbling with nitrogen, filling under nitrogen and the addition of an antioxidant. It is possible to obtain stability of longer duration, by using the procedure described, as shown by the following examples.

The antioxidant that it may be appropriate to add to the medium is a sulphite, or sulphite derivative, a thiolic substance such as, for example, cysteine, acetylcysteine, dithiothreitol or α-thioglycerol, thiomalic acid, thioglycerol, methionine; a hydroxylated substance such as ascorbic acid, iso-ascorbic acid, mannitol, sorbitol, a ethylenically unsaturated substance such as sorbic acid, undecylenic acid or fumaric acid or a hydroxy polycarboxylic acid, or a reducing sugar such as trehalulose, maltulose or isomaltulose.

Moreover, it has been found that the addition of a hydroxypolycarboxylic acid in conjunction with, or instead of the deoxygenation operation, has the effect of appreciably reducing the consumption of antioxidant and leads to a reduction in the concentration of antioxidant. The quantity of antioxidant that it may be appropriate to add is low, preferably ranging from 0,1 mg to 1 000 mg per litre of solution, and preferably from 0,2 to 20 mg.

It may also be advantageous to add a pH regulation agent, and in particular a buffering agent, especially when the easily oxidizable phenolic active principles are susceptible to being degraded or hydrolysed within particular pH ranges. It may thus be appropriate to adjust the pH of the solutions between 4 and 8 and particularly between 4.5 and 6.0 where the oxidizability of the phenolic molecules will be lower. An appropriate buffer will be, for example, a sodium hydrogenophosphate/hydrochloric acid mixture, sodium hydrogenophosphate/sodium hydroxide mixture, disodic phosphate/phosphoric acid mixture, acetic acid/sodium acetate mixture, citric acid/sodium citrate mixture, or tri-sodic citrate/hydrochloric acid mixture. The choice of pH will depend mainly on the nature of the active principle and its character of oxydizability.

The formulations according to the invention are utilized in the field of therapeutics in injectable form administered directly or added to a perfusion bag as an analgesic or an antibiotic or as a cardio-vascular drug. The injectable solution of paracetamol according to the invention is distinguished by quite remarkable analgesic properties. It may in addition contain a vasoconstrictor such as adrenalin or a central analgesic such as codeine or d-propoxyphene or an anti-inflammatory agent such as tiaprofenic acid or one of its salts.

Preparation of such a solution is carried out under nitrogen. The dissolved oxygen concentration is less than 0.05 ppm.

It is also possible to use as hydroxypolycarboxylic acid, tartaric acid or an alkaline monotartarate such as sodium salt or potassium salt in the presence of a dimetallic tartarate to obtain a pH value of the order of 5.5. It has also been noted that in the presence of hydroxypolycarboxylic acid, the pH is much more stable. The same is true for other hydroxypolycarboxylic acids such as gluconic acid, saccharic acid, citramalic acid or malic acid.

It is also possible only to use a hydroxypolycarboxylic acid salt such as trisodic citrate or disodic tartarate and adjust the pH by the moderate addition of hydrochloric acid.

The addition of hydroxypolycarboxylic acid and notably citric acid, at concentrations that make it possible to obtain a pH value of the order of 5.5, plays an important role. It has been shown that concentrations ranging from 5 to 200 mg per 100 ml ensure effective protection against oxidation (absence of coloration) and protection against degradation of the antioxidant attested by a lower content of degradation products of the cysteine used as an antioxidant.

In particular, in the case of paracetamol, after the addition of trisodic citrate at a concentration of 70 mg/100 ml of solution, the residual cysteine concentration is approximately double than that of preparations without citrate, no coloration appeared, even after 7 weeks at 40° C., and there was no variation in the concentration of paracetamol.

In conclusion, the four parameters that have to be taken into consideration as essential for preservation following heat sterilization of aqueous formulations with an active principle susceptible to oxidation are, taken separately or in combination:

complete deoxygenation by bubbling with inert gas below an oxygen concentration of less than 2 ppm, completed by the possible addition of an antioxidant, the addition of a hydroxypolycarboxylic acid, and the introduction of the aqueous solutions under an atmosphere of inert gas such as argon into a container from which the air has previously been removed.

Under these conditions, the concentration of active principle does not undergo any variation and the absence of oxidation can be established by maintaining colourless solutions for a prolonged period of time.

EXAMPLE I

Production of an Aqueous Compound of Paracetamol

A paracetamol solution is prepared in water at a concentration ranging from 2 to 50 mg/ml. Extreme deoxygenation to less than 2 ppm was carried out by bubbling with inert gas, then placing in bottles under inert gas and under vacuum (less than 65,000 Pa of residual pressure). Thus a residual concentration of oxygen is maintained in the solution, of less than 2 ppm and preferably below 1 ppm.

The pH of the solution is between 4 and 8, and preferably 4.5 to 6.0. For this purpose a buffer system is added, adjusted to 5.5.

The addition of an antioxidant contributes to the stability of the solution. The preferred antioxidants are: ascorbic acid, an ascorbate, a thiol, a polyol or a hydroxypolycarboxylic acid.

The preferred antioxidant is the cysteine sodium citrate mixture.

An isotonizing agent can be added to the solution.

EXAMPLE II

Production of an Aqueous Compound of Paracetamol without Antioxidant (Example for Comparison)

A 10 mg/ml aqueous paracetamol solution is prepared. Adjustment to pH 5.5 is carried out by the addition of HCl, and buffering by the addition of sodium hydrogenophosphate.

Deoxygenation is then carried out by bubbling with nitrogen, until a residual oxygen content of approximately 0.2 ppm is obtained. After the bottles are filled with the solution during prolonged bubbling with nitrogen, they are sterilized at 121° C. for 15 minutes.

After being kept at 25° C. for 6 months, the solution is still colourless, there is no change in the paracetamol content, and the content of degradation products of paracetamol determined by HPLC remains lower than 0.015% of the paracetamol.

In another test, the paracetamol solution, after being subjected to bubbling with nitrogen, has been packaged under nitrogen. When the bottles of solution are stoppered, a vacuum is applied, to obtain a residual pressure of less than 10,000 Pa The residual dissolved oxygen content was 0.16 ppm. After sterilization at 121° C. for 15 minutes, and after being kept for 8 days at 30° C., the solution remained colourless.

It thus appears that the essential means is deoxygenation to below a residual concentration of the order of 0.2 ppm and this means makes it possible to obtain complete preservation for a prolonged period. The possible presence of an antioxidant completes the effect of the deoxygenation but does not replace it.

EXAMPLE III

Production of an Aqueous Solution of Paracetamol Containing Citrate Ions

It has been established that aqueous solutions of paracetamol containing slightly higher residual concentrations of oxygen, i.e of the order of 0.3 to 0.4 ppm, keep less well due to the fact that the paracetamol can react with very small quantities of oxygen and can form coloured compounds.

Thus a 10 mg/ml paracetamol solution adjusted to pH 5.5 by hydrochloric acid was subjected to bubbling with nitrogen until an oxygen content of approximately 0.4 ppm was obtained. The bottles were sterilized at 121° C. for 15 minutes and kept at ambient temperature. After being kept for 9 days, a yellow-pink coloration was observed in the paracetamol solution.

Conversely, if a stabilizing agent in the form of a mixture of citric acid and sodium citrate is added to a composition identical to the above, adjustment of the pH to 5.5 occurs spontaneously and it is not necessary to add hydrochloric acid. After bubbling with nitrogen, the residual oxygen content is of the order of 0.4 ppm. Afterwards the solution is packaged into bottles under vacuum and sterilized at 121° C. for 15 minutes. The bottles are kept for 67 days at ambient temperature. The solution remains perfectly colourless.

This result is unexpected, as the action of the citrate ion cannot be related either to the antioxidants' complexing properties, nor to their reinforcing properties. Moreover, the particular effect of the citrate ion cannot be related to an antioxidizing action.

EXAMPLE IV

Stabilization of Partially Deoxygenated Aqueous Paracetamol Solutions

For greater residual oxygen contents, that may reach 1.5 ppm, it is preferable to resort to the addition of a stabilizing agent with more powerful antioxidant properties such as a sulphite, a thiol derivative or an ascorbate.

A 10 mg/ml aqueous paracetamol solution adjusted to pH 5.5 by sodium hydroxide and buffered at this value by sodium acetate was made isotonic by a sufficient quantity of sodium chloride, then an antioxidant is added to it, in this case 0.20 mg/ml cysteine chlorhydrate. This solution was subjected to bubbling with nitrogen then placed under vacuum (low pressure approx. 550 mm of Hg) before stoppering the bottles. The residual oxygen content amounted to approx. 1.5 ppm of dissolved oxygen. After sterilization, the bottles containing this solution were kept for 24 months at 25° C. The bottles remained colourless after this period, the paracetamol content was 100% of the original value, and the degradation products of the paracetamol measured by HPLC represented less than 0.02% of the paracetamol content.

The presence of an antioxidant thus played an important role. In the paracetamol solution, the antioxidant, like cysteine, reacts with the dissolved oxygen by taking the place of the phenolic molecule that is to be protected.

However, after being kept the cysteine almost completely disappeared and cystine is formed, which is the major oxidation product of cysteine.

EXAMPLE V

Buffered and Stabilized Aqueous Paracetamol Solutions

Knowing that citrate ions have a stabilizing effect with regard to paracetamol, it was desirable to check whether this effect could be explained by a protective action vis-à-vis the antioxidant, such as cysteine.

A 0.25 mg/ml aqueous cysteine solution was adjusted to pH 5.5, made isotonic by sodium chloride and buffered using as a buffering agent: dehydrated sodium citrate (0.70 mg/ml), sodium acetate, sodium hydrogenophosphate, in quantities equimolar to that of the citrate.

These solutions which involved neither bubbling with nitrogen, nor being placed under vacuum, contained approx. 7 ppm of dissolved oxygen. They were kept in darkness at 25° C. for 3 days.

The dosages carried out showed that the lowest residual cysteine content is found either in non-buffered solutions (15%), or in the presence of citrate. In contrast, in the presence of acetate (18%) or hydrogenophosphate (21%) it is higher.

It follows that the citrate ions do not have any particular protective effect vis-à-vis an antioxidant such as cysteine.

EXAMPLE VI

Preparation of Buffered Paracetamol Solutions

In this test, paracetamol, cysteine and a buffer were brought together. A quantity of sodium citrate (in the form of dihydrated disodic citrate) was added to 10 mg/ml aqueous paracetamol solutions, made isotonic by NaCl and stabilized by the addition of cysteine hydrochlorhide (0.25 mg/ml) suitable for adjusting the pH to 5.5. A quantity of citrate of the order of 0.7 mg/ml is sufficient. Comparative solutions were prepared without sodium citrate or replacing the citrate ions by equimolar quantities to those of the citrate, of either sodium acetate, or sodium hydrogenophosphate; in all cases adjusting the pH to a value of 5.5 by the addition of sodium hydroxide or hydrochloric acid.

The solutions were not subjected to bubbling with inert gas (nitrogen) and were kept in darkness at 25° C. for 3 days.

The presence of residual cysteine is thus established in increasing quantities, in the non-buffered solution (42%), in the presence of sodium acetate (17%), in the presence of sodium hydrogenophosphate (21%) and in the presence of citrate (22%) respectively.

After being kept for 20 days, all the solutions were strongly coloured with the exception of the solution containing citrate ions, which had remained colourless. It is established that in the presence of paracetamol, cysteine is protected by the presence of citrate, whilst in the absence of citrate, the cysteine has no protective effect.

Table 1 below illustrates the conclusions set forth above:

The experiments thus evidence the interactions in the presence of different oxygen contents:

| Solution | Oxygen content | Results |
|---|---|---|
| Paracetamol alone | 0.2 ppm | No degradation of the paracetamol |
| Paracetamol + citrate | 0.4 ppm | No degradation of the paracetamol |
| Paracetamol + cysteine | 1.5 ppm | No degradation of the paracetamol |
| Cysteine + citrate | 7 ppm | No protection of the cysteine |
| Paracetamol + cysteine + citrate | 7 ppm | Protection of paracetamol and cysteine |

Unexpectedly, it was by bringing together paracetamol, cysteine and citrate that the best preserving properties were obtained, both for cysteine and for paracetamol even in the presence of oxygen.

The same tests were repeated with more highly concentrated paracetamol solutions.

| Constituent | Paracetamol alone (P) | Paracetamol + citrate (PC) | Paracetamol + citrate + cysteine (PCC) |
|---|---|---|---|
| Paracetamol | 1 g | 1 g | 1 g |
| Sodium citrate | 0 | 0.070 g | qsp pH 5.5 (i.e. 0.07 g of citrate) |
| Chlorhydrate cysteine | 0 | 0 | 0.025 g |
| NaCl | 0.09 | 0.09 | 0.09 g |
| HCl or NaOH | qsp, pH 5.5 | qsp pH 5.5 | 0 |
| Inert gas | qsp $O_2$ approx. 0.5 ppm | qsp $O_2$ approx. 0.5 ppm | qsp $O_2$ approx. 0.5 ppm |
| Water | qsp 100 ml | qsp 100 ml | qsp 100 ml |

Packaging: under nitrogen (A) or under residual pressure of approx. 10,000 Pa

Sterlization at 121° C. for 15 minutes.

Results (after Sterilization):

a) the solutions P:PV (under vacuum) and PA (under nitrogen) are pink;

b) the solutions PC:PCV (citrate) are colourless and PCA (under nitrogen) is pink;

c) the solutions PCC:PCCV and PCCA are colourless but the residual cysteine content is higher when PCV is used.

Conclusion

For residual oxygen contents of the order of 0.5 ppm, the vacuum is in itself insufficient to ensure the stability of the paracetamol.

On the other hand, it acts synergically with citrate both with regard to the keeping properties of paracetamol and of cysteine.

EXAMPLE VII

Stability of Paracetamol Solution, and of Paracetamol Solution to which Sodium Citrate has been Added in the Presence of Nitrogen, or of Nitrogen Under a Vacuum Preparation of the solutions:

| Constituent | Paracetamol (P) | Paracetamol – Citrate (PC) |
|---|---|---|
| Paracetamol (mg) | 1,000 | 1,000 |
| Trisodium citrate, $2H_2O$ (mg) | — | 70 |
| NaCl (mg) | 700 | 700 |
| HCl q.s.p. pH | 5.50 | 5.50 |
| $H_2O$ q.s.p. (ml) | 100 | 100 |

The solutions are produced under nitrogen (<0,50 ppm). Filling takes place under nitrogen, of volumes of 80 ml, into 100 ml bottles. Nitrogen is bubbled into the bottle for 30 seconds before stoppering.

Half the bottles are placed under an extreme vacuum before stoppering.

The solutions are heat sterilized at +120° C. for 15 minutes.

The solutions are stabilized at +25° C. and at +40° C.

Analysis at T=0

| Solution | Oxygen (ppm) | Residual pressure in Pa | pH |
|---|---|---|---|
| Paracetamol/nitrogen, not sterilized | 0.40 | — | 5.92 |
| Paracetamol/nitrogen, sterilized | 0.34 | — | 6.03 |
| Paracetamol/vacuum, not sterilized | 0.55 | <10,000 | 5.98 |
| Paracetamol/vacuum, sterilized | 0.50 | <10,000 | 6.28 |
| Paracetamol/Citrate/Nitrogen, not sterilized | 0.50 | — | 5.50 |
| Paracetamol/Citrate/Nitrogen, sterilized | 0.60 | — | 5.53 |
| Paracetamol/Citrate/vacuum, not sterilized | 0.36 | <10,000 | 5.50 |
| Paracetamol/Citrate/vacuum, sterilized | 0.40 | <10,000 | 5.54 |

HPLC analysis does not show the presence de peaks corresponding to degradation products (<0.01%).

Appearance of the Solutions after Keeping in Darkness at 25° C. for 2 Months

| Solution | coloration on D9 | coloration on D13 | coloration on D21 | coloration on D26 | coloration at 1 month | coloration at 2 months |
|---|---|---|---|---|---|---|
| Paracetamol/ Nitrogen sterilized | colourless | colourless | yellow hue | yellow hue | yellow + | yellow + |
| Paracetamol, placed under vacuum sterilized | colourless | colourless | colourless | colourless | colourless | yellow hue |
| Paracetamol/Citrate/ Nitrogen, sterilized | colourless | colourless | colourless | yellow hue Paracetamol/ Nitrogen | yellow hue | yellow + |
| Paracetamol/Citrate/ placed under vacuum, sterilized | colourless | colourless | colourless | colourless | colourless | colourless |

Conclusion

Only the citrate+vacuum combination ensures complete preservation of the paracetamol.

EXAMPLE VIII

Stability of the Paracetamol Solutions Protected by Sodium Citrate and Cysteine for Oxygen Concentrations of Approx. 1 ppm Composition of the Solution

| Constituent | Quantity |
|---|---|
| Paracetamol (g) | 1 |
| Cysteine HCL, H20 (mg) | 25 |
| Sodium citrate, H20 (mg) | 70 |
| Sodium chloride (mg) | 700 |
| Water enough for | 100 ml |

Preparation of the solution takes place with continuous bubbling with nitrogen. It is filled into 100 ml bottles, under nitrogen, until a solution containing between 0.7 and 1.0 ppm of oxygen is obtained.

The bottles are then stoppered under a nitrogen atmosphere or under vacuum (approx. 10,000 Pa). Following sterilization at 121° C. for 15 minutes, the bottles are kept in darkness at 40° C. The colouration, the pH, the oxygen content and the residual cysteine content are evaluated immediately after sterilization, then after being stored for 14 days.

Results

| Solution | Coloration | pH | Oxygen (ppm) | Residual cysteine (%) |
|---|---|---|---|---|
| Solution under nitrogen, after sterilization | colourless | 5.53 | 0.85 | 75 |
| Solution under vacuum, after sterilization | colourless | 5.51 | 0.90 | 85 |
| Solution under nitrogen, after 14 days at 40° C. | yellow | 5.58 | 0.60 | 27 |
| Solution under vacuum, after 14 days at 40° C. | colourless | 5.59 | 0.90 | 85 |

Conclusion

Keeping under vacuum has a protective effect on the Paracetamol and the cysteine when the solution is kept under conditions of accelerated degradation. Conversely, preservation is insufficient under nitrogen. The vacuum seems to inhibit the oxidation reaction of the paracetamol and the cysteine, which confirms the reduction in residual oxygen under nitrogen, as compared with the maintenance of residual oxygen under vacuum.

EXAMPLE IX

1% Dobutamine Sulphate Solution

A Dobutamine sulphate solution is prepared by dissolving 1 g Dobutamine in 50 ml of water and 19 ml of a 0.10% sodium ascorbate solution is added, with continuous bubbling of nitrogen. Then 25 mg hydrated cysteine chlorhydrate and 70 mg hydrated sodium citrate are added, then 700 mg sodium chloride to ensure isotonicity. The solution is made up to 100 ml by the addition of distilled water for injectable preparations.

It is filled into 100 ml bottles under nitrogen until the residual oxygen content is below 0.8 ppm. The bottles are then stoppered under vacuum (approx. 10,000 Pa) and sterilized at 121° C. for 20 minutes.

After removal from the autoclave, the bottles are kept in darkness in a thermostatic cupboard at 50° C.

An evaluation is made of absorption at 308 nm as an indication of oxidation into secondary products, the residual oxygen content and the residual cysteine content immediately after sterilization, then after being kept for 14 days at 50° C.

Results

There is no degradation of the Dobutamine in heat.

Using liquid chromatography the appearance of secondary peaks is established, detected by measuring the absorption at 308 nm, the degree of which decreases as the pH increases. Coloration remains slight and reduces as the pH increases.

What is claimed is:

1. A method for preparing an aqueous solution with an active nature susceptible to oxidation, which is paracetamol, while preserving for a prolonged period, comprising deoxygenation of the solution by bubbling with at least one inert gas and/or placing under vacuum, until the oxygen content is below 2 ppm, and optionally the aforementioned aqueous solution with an active principle is topped with an inert gas atmosphere heavier than air and placed in a closed container in which the prevailing pressure is 65,000 Pa maximum, and the oxygen content of the aqueous solution is below 2 ppm, and optionally the deoxygenation of the solution is completed by addition of an antioxidant.

2. The method for preparing a formulation of claim 1 wherein deoxygenation of the solution is completed by addition of a hydroxypolycarboxylic acid.

3. The method for preparing a formulation of claim 1 wherein the residual oxygen content of the aqueous solution is below 1 ppm.

4. The method for preparing a formulation of claim 1 wherein the residual oxygen content in the aqueous solution is equal to 0.5 ppm or below.

5. The method for preparing a formulation of claim 2 wherein the hydroxypolycarboxylic acid is selected from the group consisting of citric acid, tartaric acid, gluconic acid, saccharic acid, citramalic acid and malic acid.

6. The method for preparing a formulation of claim 2 wherein the hydroxypolycarboxylic acid is an acid or a salt thereof.

7. The method for preparing a formulation of claim 2 wherein the concentration of hydroxypolycarboxylic acid and/or one of its salts is 5 to 200 mg/100 ml of aqueous solution.

8. The method for preparing a formulation of claim 1 wherein the antioxidant is selected from the group consisting of thiols, derivatives of ascorbic acid and reducing sugars.

9. The method for preparing a formulation of claim 1 wherein the antioxidant is ascorbic acid or isoascorbic acid.

10. The method for preparing a formulation of claim 1 wherein the antioxidant is a mixture of cysteine and sodium citrate.

11. The method for preparing a formulation according to claim 1 comprising subjecting an aqueous solution containing at least one phenolic active principle which is paracetamol, to which an antioxidant and a hydroxypolycarboxylic acid optionally have been added to extreme deoxygenation; introducing under an inert gas atmosphere, part or all of the deoxygenated aqueous solution into a container previously cleared of the air contained therein; then stoppering the container under an inert gas atmosphere, to create, in the closed container, a maximum pressure of 65,000 Pa to obtain an aqueous solution with a phenolic acid principle in a placed closed container, in which the oxygen content is below or equal to 2 ppm.

12. The method of claim 10 wherein the deoxygenation is achieved by bubbling with an inert gas.

13. The method of claim 10, wherein the deoxygenation is achieved by application of vacuum.

14. The method of claim 10 wherein after stoppering, the solution is subjected to sterilization.

15. The method of claim 10 wherein the aqueous solution with an oxidizable active principle is subjected to sterilizing filtration under inert gas.

16. The method of claim 10 wherein the inert gas used for bubbling is nitrogen.

17. The method of claim 10 wherein the inert topping gas is heavier than air.

18. The method of claim 10 wherein the container is cleared of the air contained therein, by insufflation with an inert gas.

19. An injectable aqueous solutions containing, as an active ingredient, a principle of phenolic nature susceptible to oxidation, preserved by the method of claim 1.

* * * * *

UNITED STATES PATENT AND TRADEMARK OFFICE
CERTIFICATE OF CORRECTION

PATENT NO. : 6,992,218 B2  
APPLICATION NO. : 10/332060  
DATED : January 31, 2006  
INVENTOR(S) : Francois Dietlin and Daniele Fredj Page 1 of 1

It is certified that error appears in the above-identified patent and that said Letters Patent is hereby corrected as shown below:

Col. 12, line 54 in claim 1, "active nature" should read -- active principle of phenolic nature --.

Signed and Sealed this

First Day of September, 2009

David J. Kappos  
*Director of the United States Patent and Trademark Office*

(12) EX PARTE REEXAMINATION CERTIFICATE (10694th)

United States Patent
Dietlin et al.

(10) Number: US 6,992,218 C1
(45) Certificate Issued: Aug. 27, 2015

(54) METHOD FOR OBTAINING AQUEOUS FORMULATIONS OF OXIDATION-SENSITIVE ACTIVE PRINCIPLES

(75) Inventors: Francois Dietlin, La Vesinet (FR); Daniele Fredj, Gif sur Yvette (FR)

(73) Assignee: PHARMATOP SCR, Le Chesnay (FR)

Reexamination Request:
No. 90/013,107, Jan. 8, 2014

Reexamination Certificate for:
Patent No.: 6,992,218
Issued: Jan. 31, 2006
Appl. No.: 10/332,060
PCT Filed: Jun. 6, 2001
PCT No.: PCT/FR01/01749
§ 371 (c)(1),
(2), (4) Date: Aug. 4, 2003
PCT Pub. No.: WO01/93830
PCT Pub. Date: Dec. 13, 2001

Certificate of Correction issued Sep. 1, 2009

(30) Foreign Application Priority Data

Jun. 6, 2000 (FR) ..................... 00 07231

(51) Int. Cl.
*C07C 209/90* (2006.01)
*A61K 9/00* (2006.01)
*B01D 19/00* (2006.01)
*A61K 47/22* (2006.01)
*A61K 47/12* (2006.01)
*A61K 31/05* (2006.01)
*A61K 31/136* (2006.01)
*A61K 31/167* (2006.01)
*A61K 31/375* (2006.01)
*A61K 33/00* (2006.01)
*A61K 45/06* (2006.01)

(52) U.S. Cl.
CPC ............... *A61K 9/0019* (2013.01); *A61K 9/008* (2013.01); *A61K 31/05* (2013.01); *A61K 31/136* (2013.01); *A61K 31/167* (2013.01); *A61K 31/375* (2013.01); *A61K 33/00* (2013.01); *A61K 45/06* (2013.01); *A61K 47/12* (2013.01); *A61K 47/22* (2013.01); *B01D 19/0005* (2013.01); *A61K 2300/00* (2013.01)

(58) Field of Classification Search
None
See application file for complete search history.

(56) References Cited

To view the complete listing of prior art documents cited during the proceeding for Reexamination Control Number 90/013,107, please refer to the USPTO's public Patent Application Information Retrieval (PAIR) system under the Display References tab.

*Primary Examiner* — Dwayne C. Jones

(57) ABSTRACT

A method for obtaining aqueous formulations with easily oxidizable active principles, notably phenols, stable over a prolonged period, comprising subjecting them to extreme deoxygenation by bubbling with an inert gas and/or placing wider vaccum, protecting them against possible resorption of oxygen by keeping them under an inert gas atmosphere, by filling, under inert gas, into bottles previously cleared of air by insufflation with inert gas, then subjecting them, while stoppering, to low pressure as obtained in the bottle, of 65,000 Pa maximum, to obtain aqueous solutions having a residual oxygen concentration in the solution below 2 ppm, and preferably of the order of 1 ppm and even 0.5 ppm useful as injectable preparations having an oxygen concentration in the solution below 2 ppm.

Attention is directed to the decision of The Federal Circuit's Decision dated March 23, 2015 in *Cadence Pharma. Inc. et al.* v. *Exela Pharmsci Inc. et al.*, Case No 2014-1184. This reexamination may not have resolved all questions raised by this decision. See 37 CFR 1.552(c) for *ex parte* reexamination and 37 CFR 1.906(c) for *inter partes* reexamination.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-10 and 12-19 is confirmed.

Claim 11 is determined to be patentable as amended.

New claims 20-25 are added and determined to be patentable.

11. The method for preparing a formulation according to claim 1 comprising subjecting an aqueous solution containing at least one phenolic active principle which is paracetamol, to which an antioxidant and a hydroxypolycarboxylic acid optionally have been added to extreme deoxygenation; introducing under an inert gas atmosphere, part or all of the deoxygenated aqueous solution into a container previously cleared of the air contained therein; then stoppering the container under an inert gas atmosphere, to create, in the closed container, a maximum pressure of 65,000 Pa to obtain an aqueous solution with a phenolic acid principle in a placed closed container, in which the oxygen content is below [or equal to] 2 ppm.

20. *The method of claim 1 wherein the residual oxygen content is 0.5 to 1 ppm.*

21. *The method of claim 1 wherein the residual oxygen content is equal to or below 0.5 ppm.*

22. *The method of claim 1 wherein the residual oxygen content is equal to or below 0.05 ppm.*

23. *The method of claim 1 wherein the residual oxygen content is selected from the group consisting of 0.16 ppm, 0.2 ppm, 0.3 ppm, 0.4 ppm, 0.5 ppm, 0.6 ppm, 0.7 ppm, 0.8 ppm, 0.9 ppm and 1 ppm.*

24. *The method of claim 1 wherein the formulation is colorless.*

25. *The method of claim 2 wherein the hydroxypolycarboxylic acid is selected from the group consisting of citric acid, tartaric acid, gluconic acid, saccharic acid, citramalic acid and malic acid.*

\* \* \* \* \*